United States Patent
Jung et al.

(10) Patent No.: US 8,545,768 B2
(45) Date of Patent: Oct. 1, 2013

(54) TEST SENSOR PACKAGE

(75) Inventors: Sung-Kwon Jung, Granger, IN (US);
Steven C. Charlton, Osceola, IN (US);
Suny J. George, Granger, IN (US);
Andrew J. Dosmann, Granger, IN (US);
Karen L. Marfurt, Edwardsburg, MI (US)

(73) Assignee: Bayer HealthCare LLC, Tarrytown, NY (US)

( * ) Notice: Subject to any disclaimer, the term of this patent is extended or adjusted under 35 U.S.C. 154(b) by 582 days.

(21) Appl. No.: 12/875,310

(22) Filed: Sep. 3, 2010

(65) Prior Publication Data
US 2010/0329951 A1    Dec. 30, 2010

Related U.S. Application Data

(63) Continuation of application No. 11/795,843, filed as application No. PCT/US2006/003435 on Jan. 31, 2006, now abandoned.

(60) Provisional application No. 60/649,046, filed on Feb. 1, 2005.

(51) Int. Cl.
*G01N 31/22* (2006.01)
*G01N 33/52* (2006.01)

(52) U.S. Cl.
USPC ........ 422/430; 422/401; 422/100; 422/82.05; 422/68.1

(58) Field of Classification Search
USPC ............................ 422/56, 58, 82.05, 401, 430
See application file for complete search history.

(56) References Cited

U.S. PATENT DOCUMENTS

| | | | |
|---|---|---|---|
| 5,100,620 | A | 3/1992 | Brenneman |
| 5,223,219 | A | 6/1993 | Subramanian et al. |
| 5,281,395 | A | 1/1994 | Markart et al. |
| 5,427,953 | A | 6/1995 | Yee |
| 5,630,986 | A | 5/1997 | Charlton et al. |
| 5,854,074 | A | 12/1998 | Charlton et al. |
| 6,099,802 | A * | 8/2000 | Pugh ............................. 422/401 |
| 6,200,773 | B1 | 3/2001 | Ouyang et al. |
| 6,541,216 | B1 | 4/2003 | Wilsey et al. |
| 2003/0059350 | A1 | 3/2003 | Sacherer |

FOREIGN PATENT DOCUMENTS

| | | |
|---|---|---|
| EP | 0 877 250 A2 | 11/1998 |
| EP | 0 990 706 A1 | 4/2000 |
| EP | 1 285 695 A2 | 2/2003 |
| EP | 1 285 695 A3 | 2/2003 |
| EP | 0 877 250 B1 | 12/2003 |

OTHER PUBLICATIONS

International Search Report, corresponding to International Patent Application No. PCT/US2006/003435, dated Sep. 15, 2006; 6 pages.

(Continued)

*Primary Examiner* — Sally Merkling
(74) *Attorney, Agent, or Firm* — Nixon Peabody LLP (57) ABSTRACT

A fluid sensor comprises a formed plastic body and a reagent. The body has a top face with an integral first surface. The body also has a bottom face opposed to the first surface and a sidewall that extends from the periphery of the top face. The first surface is adapted to accept a fluid sample. The reagent is disposed on the integral first surface and causes a color change detectable on the bottom face when the reagent reacts with an analyte in the fluid sample.

12 Claims, 5 Drawing Sheets

(56) References Cited

OTHER PUBLICATIONS

European Extended Search Report, European Application No. 10175005.7 dated Nov. 25, 2010, 6 pages.

Written Opinion of the International Search Authority corresponding to International Patent Application No. PCT/US2006/003435, dated Sep. 15, 2006; 8 pages.

* cited by examiner

TEST SENSOR PACKAGE

CROSS-REFERENCE TO RELATED APPLICATIONS

This application is a continuation of U.S. application Ser. No. 11/795,843, filed Jul. 23, 2007, which was the National Stage of International Application No. PCT/US06/03435, filed Jan. 31, 2006, which claims the benefit of U.S. Provisional Application No. 60/649,046, filed on Feb. 1, 2005, all of which are incorporated by reference in their entireties.

TECHNICAL FIELD

The present invention relates to a fluid monitoring system, and more particularly, to a new and improved sensor and package that is used in analyzing blood glucose or other analytes contained therein.

BACKGROUND

Those who have irregular blood glucose concentration levels are medically required to regularly self-monitor their blood glucose concentration level. An irregular blood glucose level can be brought on by a variety of reasons including an illness such as diabetes. An estimated 18 million people are afflicted with diabetes in the United States alone. A diabetic patient typically monitors his or her blood glucose concentration level to determine whether the level is too high or too low, and whether any corrective action, such as administering insulin or other medication, is necessary to bring the level back within a normal range. The failure to take corrective action can have serious implications. When blood glucose levels drop too low—a condition known as hypoglycemia—a person may become nervous, shaky, confused, have an impaired judgment, and eventually pass out. A person can also become very ill if their blood glucose level becomes too high—a condition known as hyperglycemia. Both hypoglycemia and hyperglycemia can potentially be life-threatening emergencies. As a result, a diabetic may require frequent sampling of his or her blood glucose—typically several times per day.

In one type of blood glucose testing system, sensors are used to test a sample of blood. Such a sensor may contain bio-sensing or reagent material that will react with blood glucose. The testing end of the sensor is adapted to be placed into the fluid being tested, for example, blood that has accumulated on a person's finger after the finger has been pricked. In one type of sensor, for example in U.S. Pat. No. 5,100,620, issued Mar. 31, 1992, and entitled Capillary Tube/Gap Reagent Format, the fluid is drawn into a capillary channel that extends in the sensor from the testing end to the reagent material by capillary action so that a sufficient amount of fluid to be tested is drawn into the sensor. For electrochemical sensors, the fluid then chemically reacts with the reagent material in the sensor. The chemical reaction results in an electrical signal indicative of the blood glucose level in the blood being tested, which is then supplied to contact areas located near the rear or contact end of the sensor. For optically read or photometric sensors, a reflectance reading can determine the color change indicative of the glucose concentration in the blood/reagent mixture.

As with all medical diagnostic devices, contamination is of major concern. It is necessary to avoid contamination of both equipment and personnel by fluids, and to avoid contamination of a patient with fluids from others. For photometric blood glucose monitors in particular, a major concern is contamination of the read-head by blood. Blood on the optical read-head can give rise to erroneous measurements. To address this problem, current sensors have been designed so that they are inoculated with a patient's blood before the sensor is placed in the meter. While this configuration reduces the risk of contamination for the patient, the meter can still become contaminated with blood. In addition, this process is less convenient for the user.

To address the risk of meter contamination, some sensors have been designed to include a reactive membrane stretched across a through opening in a shaped sensor tip. While such sensors reduce the risk of meter contamination over conventional sensors, there still remains the risk that the read-head of the meter can become contaminated. The reactive membrane does not completely cover the through opening, allowing the possibility that blood may leak onto the meter or read-head either through the membrane or around the membrane/through opening juncture.

Manufacturing cost is another concern that exists with sensors that include a reactive membrane stretched across a through opening. Due to the large number of sensors a diabetic may use, even a minor reduction in the manufacturing cost of a sensor can result in substantial savings to the diabetic end user. Applying a separate membrane to a through opening involves extra manufacturing steps of handling a separate membrane and applying the membrane to the sensor base.

In addition to cost, reducing the sample volume is another concern that exists for current sensors. Current sensors require sample volumes anywhere from approximately 0.3 µL to 10.0 µL of blood. For example, in conventional capillary fill sensors, it is difficult to get a reasonable separation between the sample application point on the sensor and the read-head. To illustrate this, if the sensor protrudes 0.3 inches from the meter and the read-head is located 0.2 inches inside the meter case, then the capillary must be 0.5 inches long. Aside from resulting in a considerable waste of sample, this can also lead to a slow fill time and require larger punctures to extract the necessary quantity of blood.

Another challenge with current sensors is their packaging. Before use, the sensors need to be maintained at an appropriate humidity level so as to insure the integrity of the reagent materials in the sensor. Sensors can be packaged individually in tear-away packages so that they can be maintained at the proper humidity level. For instance, blister-type packaging methods have often been used. The packages can include desiccant material to maintain the proper humidity in the package. In order for a person to use an individual sensor for testing blood glucose, the package must be opened by tearing the seal. Alternatively, some packages require the user to exert force against one side of the package resulting in the sensor bursting or rupturing the foil on the opposite side. As can be appreciated, the opening of these packages can be difficult and may result in damage to the sensor. Moreover, once the package is opened the user needs to be sure that the sensor is not damaged or contaminated as it is being placed into the sensor holder and used to test the blood sample.

Other sensor packages, such as the one used in U.S. Pat. No. 5,630,986, issued May 20, 1997, and entitled Dispensing Instrument for Fluid Monitoring Sensors, also maintain a low humidity environment, but they are not easy to manufacture. One reason is that the symmetry of the circular packaging array does not match the rectangular symmetry of standard sheet sensor printing processes, necessitating handling individual sensors during packaging. The meter is also mechanically complex because of the mechanism required to extract the sensor from the blister pack. In addition, the number of sensors is not visible at a glance.

For the foregoing reasons, there is a need for a blood glucose sensor that reduces the risk of contamination, the manufacturing cost, and the sample volume. Further, there is a need for a package for such a blood glucose sensor that maintains the sensors at the proper humidity, is simple to use, and has a visual display of the remaining sensors.

BRIEF SUMMARY

Accordingly, an object of the present invention is to provide a new and improved sensor and package used in testing blood glucose. In particular, objects of the present invention are to provide a new and improved blood glucose sensor and package made from a one-piece formed body with a reagent applied to the sensor, and which overcomes the problems or limitations discussed above.

In accordance with these and other objects of the present invention, the present invention is embodied in a fluid sensor that comprises a formed plastic body and a reagent. The body has a top face with an integral first surface. The body also has a bottom face opposed to the first surface and a sidewall that extends from the periphery of the top face. The first surface is adapted to accept a fluid sample. The reagent is disposed on the integral first surface and causes a color change detectable on the bottom face when the reagent reacts with an analyte in the fluid sample.

In a second embodiment of the present invention, a fluid sensor comprises a formed porous plastic body, a surfactant, and a reagent. The body has a top face with an integral first surface, a bottom face with a second surface opposed to the first surface, and a sidewall adjacent to the top face. The first surface is adapted to accept a fluid sample. The surfactant is disposed on the body. The reagent causes a color change detectable on the second surface when the reagent reacts with an analyte in the fluid sample.

In accordance with a third aspect of the present invention, the present invention is embodied in a blood glucose sensor kit comprising a sensor package, a blood glucose meter, and a guide. The sensor package includes a base portion having at least one sensor cavity and at least one desiccant cavity in fluid communication with the sensor cavity. The sensor package also includes a desiccant material in the desiccant cavity and a protective sheet covering the sensor cavity and the desiccant cavity. The sensor package also includes a sensor located in the sensor cavity. The blood glucose meter has a housing, a display disposed on the housing, and a read-head disposed on the housing, in which the read-head is adapted to detachably engage the sensor. The guide is adapted to cover the protective sheet. The guide also has at least one opening adapted to align the read-head to engage the sensor within the sensor cavity.

According to a fourth aspect of the present invention, a blood glucose sensor kit comprises a sensor package and a blood glucose meter. The sensor package includes a container having an inner surface, a desiccant liner disposed in the container, a friction liner disposed in the container, and at least one sensor located in the container, frictionally engaging the friction liner. The blood glucose meter has a housing with a display and a read-head disposed on the housing. The read-head is adapted to detachably engage the sensor while the sensor is located in the sensor package.

According to a fifth aspect of the present invention, a blood glucose sensor package comprises a container, a desiccant liner, a friction liner, a first sensor, and a cover. The container has an inner surface. The desiccant liner is disposed in the container. The friction liner is disposed in the container. The first sensor is located in the container and frictionally engages the friction liner. The cover seals the container.

According to a sixth aspect of the present invention, a method of making a fluid sensor includes the act of forming a plastic body. The plastic body has a top face with an integral first surface, a bottom face opposed to the first surface, and a sidewall extending from the periphery of the top face. The first surface is adapted to accept a fluid sample. The method also includes the act of applying a reagent to the integral first surface. The reagent causes a color change detectable on the bottom face when the reagent reacts with an analyte in the fluid sample. The method also includes the act of applying a lid to a raised region on the top face.

DETAILED DESCRIPTION OF THE DRAWINGS AND THE PRESENTLY PREFERRED EMBODIMENTS

Figure 1:
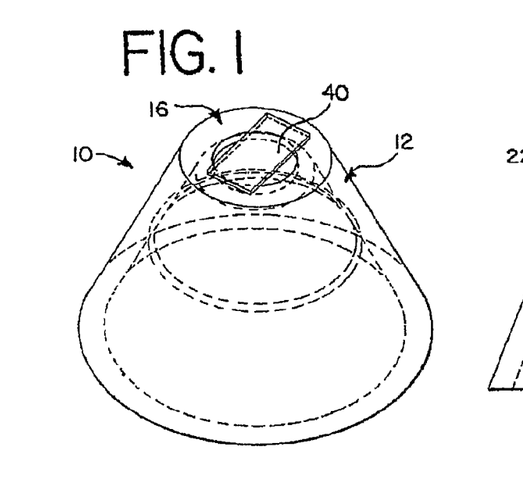
FIG. 1 is a perspective view of a blood glucose sensor constituting one embodiment of the present invention.
Figure 2:
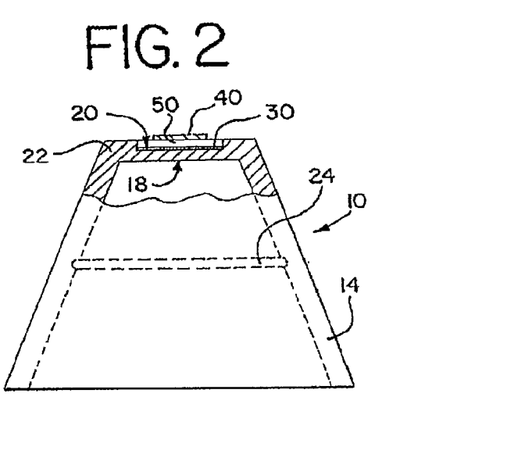
FIG. 2 is a partial cross-section view of the blood glucose sensor of FIG. 1.

Referring now more specifically to the drawings, therein is disclosed a fluid sensor generally designated by the reference numeral 10 and embodying the present invention. As illustrated in FIGS. 1-2, one embodiment of the sensor 10 includes a body 12, a reagent 30, and a lid 40.

Figure 9:
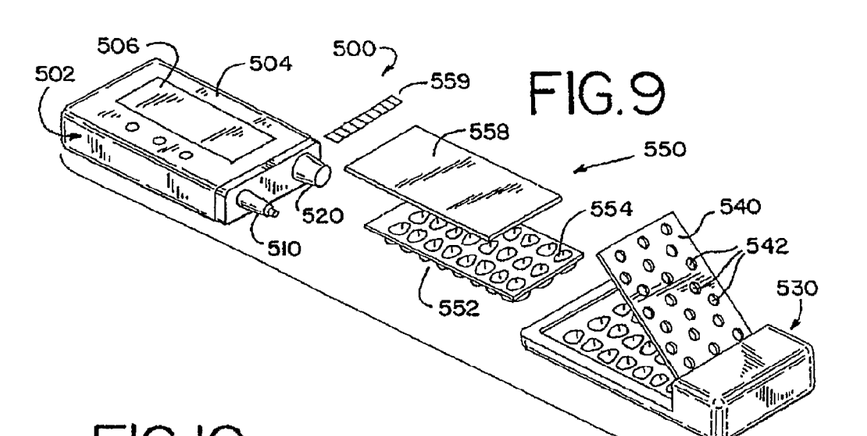
FIG. 9 is an exploded perspective view of a blood glucose kit.
Figure 11:
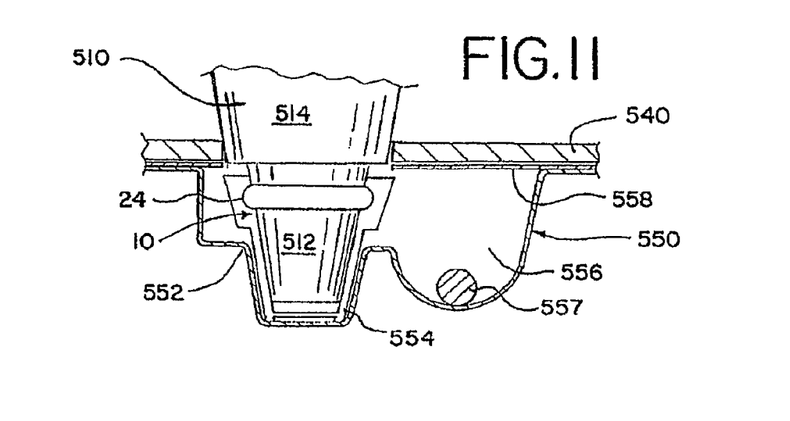
FIG. 11 is a partial cross-section view of a read-head of a blood glucose meter inserted into the sensor of FIG. 7 contained within a sensor package.

The body 12 may be formed into a hollow frustum (such as a conical or pyramidal shape) shaped to mount on an optical read-head 510 of corresponding shape (FIGS. 9 and 11). The read-head 510 can host two light guides, one for a light source and another for reflected light. Body 12 may be formed from impermeable plastic such as polypropylene, polyethylene terephthalate, or other plastic, using techniques known in the art, such as film forming, injection molding, etc. The frustum shaped body 12 has only one open end, with integral sidewalls 14 that extend downward from the periphery of a top face 16. A bottom face 18 is located on the inside of body 12, opposite top face 16. Body 12 may be sized with an overall height of 0.2 inches, although other heights that are sufficient to avoid contamination of a glucose meter 502 by sample blood may also be used.

The engagement of body 12 with the read-head 510 can be facilitated by a first latch 24 located on the sidewall 14 of the sensor. The latch 24 may be formed using any technique known in the art and may comprise any number of shapes, such as indentations, holes, grooves, or embosses in the sidewall 14 of body 12.

The top face 16 has a raised region forming a spacer 22 that surrounds an integral first surface 20, which may be formed into a concave or recessed surface for ergonomic sample loading. In the embodiment shown in FIGS. 1-2, spacer 22 is depicted as an annulus, although other shapes may be used. Spacer 22 may be integrally formed with body 12. Alternately, spacer 22 may be formed as a separate molded spacer and attached to the top face 16 of body 12 through sonic welding, an adhesive, or other method of attachment.

Lid 40 is mounted to spacer 22 on the top face 16 of body 12, forming a capillary chamber 50. As best seen in FIG. 1, this arrangement has open sides formed by the gap between lid 40 and first surface 20 so as to provide access by a blood sample to the capillary chamber 50. Capillary chamber 50 allows for a controlled sample volume of blood to react with reagent 30. FIGS. 1 and 2 illustrate one embodiment where lid 40 is constructed of a rectangular strip of impermeable plastic, formed in a similar manner to body 12 described above. However, lid 40 is preferably colored to form an opaque barrier as described below. In addition, other shapes for lid 40, such as a circle, square, etc. may also be used. Similarly, spacer 22 may be formed such that it is only under the lid 40, and does not form a complete raised ring around top face 16 of body 12. Lid 40 may be attached to spacer 22 through sonic welding, an adhesive, or other attachment method.

Reagent 30 is applied to the first surface 20 such that when a droplet of blood is applied to first surface 20, the blood reacts with the reagent 30. Reagent 30 causes a color change that can be detected by read-head 510 from bottom face 18. As a result, top face 16 of body 12 is colored to allow sufficient light to be transmitted from first surface 20 to bottom face 18. For example, top face 16 may have a translucent or transparent coloring. To reduce manufacturing costs, reagent 30 may be applied directly to the plastic of body 12 through a coating, screen, or stencil-printing process. Alternatively, methods such as pipetting, pump deposition, or pin deposition can be used. If the reagent 30 is applied to the first surface 20 through pipetting or pump or pin deposition, improved results may be obtained if the reagent accepting surface has an area defined by a raised mesa. Reagent 30 may also be membrane-based, however, in another embodiment.

The reagent 30 may be made from any of a number of compositions that are capable of generating detectable specie that can be measured by a change in reflectance. One such reagent composition is a glucose dehydrogenase (GDH)—pyrroloquinoline quinone (PQQ) based system. Such a reagent system is described as follows:

1) glucose+GDH-PQQ (oxidized state)→gluconolactone+GDH-PQQ (reduced state)
2) electron transferring mediator (oxidized state)+GDH-PQQ (reduced state)→electron transferring mediator (reduced state)+GDH-PQQ (oxidized state)
3) electron transferring mediator (reduced state)+tetrazolium→electron transferring mediator (oxidized state)+formazan The intensity of the color of formazan, which is measured by a photometric sensor (not shown) in read-head 510, is a function of the concentration of glucose. Alternatively, a GDH and diaphorase based system can be used. Such a system is described as follows:

1)

$$\text{glucose} + \text{NAD}^+ \text{ (nicotinamide adenine dinucleotide)} \xrightarrow{\text{GDH}} \text{NADH} + \text{H}^+ + \text{gluconolactone}$$

2)

$$\text{NADH} + \text{tetrazolium} \xrightarrow{\text{Diaphorase}} \text{NAD}^+ + \text{formazan}$$

The reagent 30 compositions can be deposited onto the first surface 20 of body 12 in a matrix, such as a titanium dioxide and polymer (e.g., polyacrylic) matrix, according to any of the methods described above.

In operation, the sensor 10 is mounted to read-head 510 on the blood glucose meter 502. Blood glucose meter 502 (seen in FIG. 9) takes an initial reflectance reading on sensor 10 prior to the application of a blood sample to the sensor 10. This initial reading serves to correct for variations in background color and sensor positioning. A user is then prompted to apply a blood sample to lid 40. The blood sample is drawn by capillary action into capillary chamber 50 to react with reagent 30. After a predetermined period of time, blood glucose meter 502 then takes another reflectance reading of sensor 10. This reflectance reading of reagent 30 on sensor 10 measures the color change of formazan or other detectable specie, which indicates the glucose concentration in the blood/reagent mixture.

Because the detectable specie generated from the analyte is measured by a change in reflectance, a significant fraction of light is transmitted through the reagent 30 where it can be lost or returned to the read-head 510 by scattering from the blood sample. The amount of light scattering depends on the sample volume and hematocrit, which may lead to inaccuracies in the reflectance measurement. Further, if the blood volume sample above the reagent 30 is not defined, the conversion reaction continues past the ideal test time. This leads to drifting of the result. Capillary chamber 50 is designed to serve as a reaction cell, providing a defined volume and surface on the side opposing the reagent 30. In addition, lid 40 preferably has an opaque coloration to provide a defined and consistent reflective background.

Figure 16:
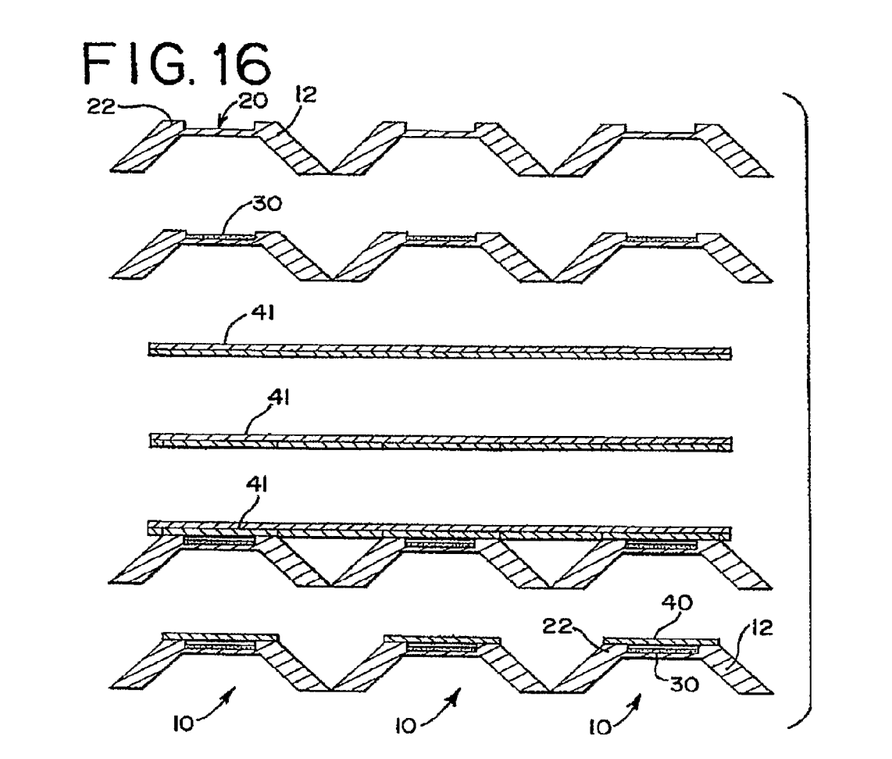
FIG. 16 is a cross-section view of an array of the blood glucose sensors of FIG. 1, illustrating a sequence of steps in the typical construction of the sensors with integral spacers.
Figure 17:
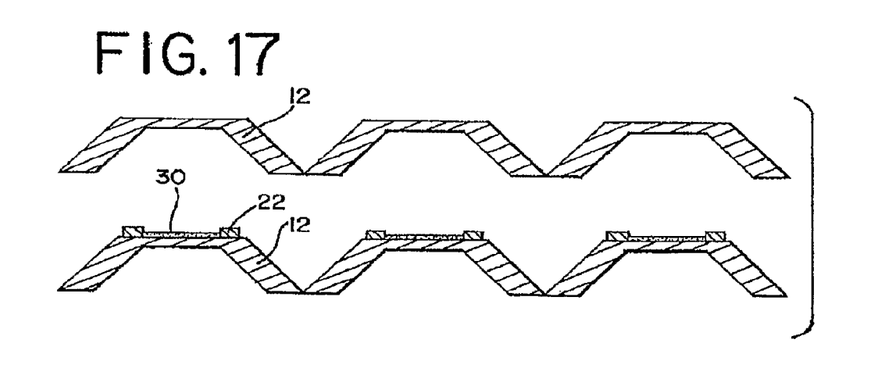
FIG. 17 is a cross-section view of an array of the blood glucose sensors in FIG. 3, illustrating a sequence of steps in the typical construction of the sensors with spacers made by printing.

FIGS. 16 and 17 illustrate two construction methods for an array of sensors 10 with capillary chambers 50 as described above. In FIG. 16, the spacer 22 is integrally molded with the body 12. The reagent 30 is then applied to the first surface 20, in the area between spacer 22, as described above. The lid 40 is applied next. The surface of the lid 40 that faces the inside of the capillary chamber can be optimized for rapid filling and may also be a heat-activated adhesive, such as U53 water dispersible polyurethane available from Bayer Corporation of Elkhart, Ind., United States of America. This lid formulation is known as ROA. The lid is temporarily mounted to a backing adhesive 41 and die-cut in this form, through the ROA but leaving the temporary backing 41 intact. This structure is aligned over the tips as shown and heated through the temporary backing 41 to adhere the ROA adhesive to the spacers 22 of the sensor 10. Finally the temporary backing 41 is removed leaving completed sensors 10.

FIG. 17 shows a variation of the construction method depicted in FIG. 16. Body 12 is molded without an integral spacer 22. The flat top of the body 12 is advantageously suited for screen or stencil-printing the spacer 22. Alternatively, spacer 22 may be made in a printing step. To avoid a heat sealing step when applying the lid 40, a hydrophilic pressure-sensitive adhesive may be used instead.

Figure 3:
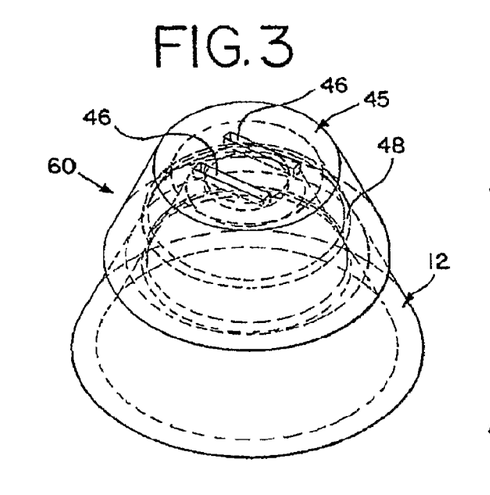
FIG. 3 is a perspective view of a blood glucose sensor constituting a second embodiment of the present invention.
Figure 4:
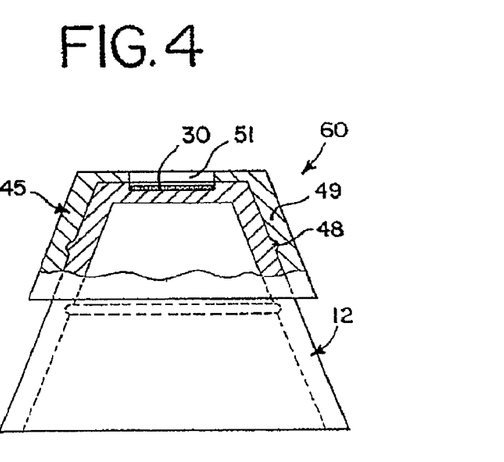
FIG. 4 is a partial cross-section view of the blood glucose sensor of FIG. 3.

Another embodiment of a sensor 60 is illustrated in FIGS. 3 and 4. Sensor 60 includes body 12, reagent 30, and a sensor lid 45. Sensor lid 45 may be formed from impermeable plastic as a hollow frustum, similar to body 12, as described above. Sensor lid 45 may be attached to body through a second latch 48 located on a sidewall 49 of sensor lid 45. The second latch 48 may comprise any technique known in the art, such as indentations, holes, grooves, or embosses. Alternately, sensor lid 45 may be attached to body 12 through sonic welding, an adhesive, or another attachment method. Vent holes 46 are formed in sensor lid 45 to allow a blood sample to flow into capillary chamber 51 and air to flow out of chamber 51 formed by the sensor lid 45 and the body 12. Other aspects of the sensor 60 are similar to the sensor 10 shown in FIGS. 1 and 2 and described above.

Figure 5:
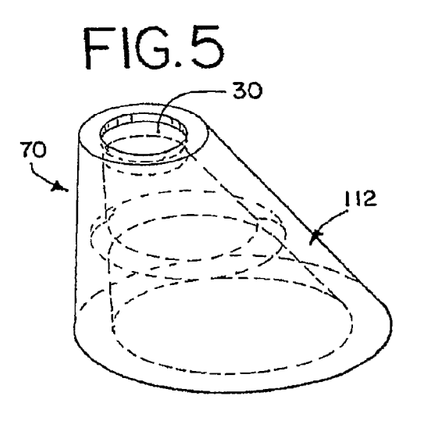
FIG. 5 is a perspective view of a blood glucose sensor constituting a third embodiment of the present invention.
Figure 6:
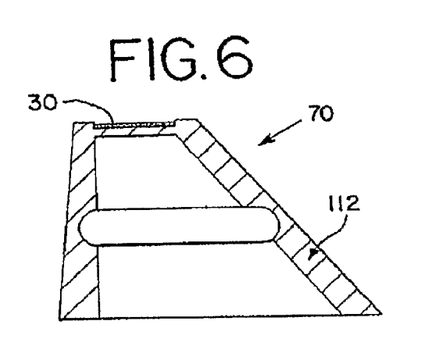
FIG. 6 is a cross-section view of the blood glucose sensor of FIG. 5.

Another embodiment of a sensor 70 is illustrated in FIGS. 5 and 6. Sensor 70 is made up of a body 112 and reagent 30, but does not include a lid or sensor lid (as those components are described in connection with the embodiments of FIGS. 1-4). Although a significant fraction of light may be lost and the blood volume sample above the reagent 30 may not be defined, blood glucose meter 502 may be adapted to correct for this by taking additional reflectance readings or with some other correction. Other aspects of sensor 70 are similar to the sensor 10 shown in FIGS. 1 and 2 and described above.

Figure 7:
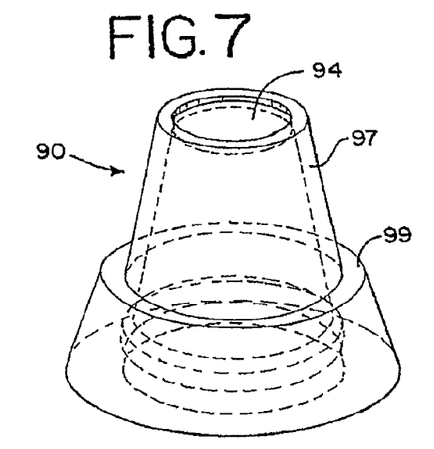
FIG. 7 is a perspective view of a fourth embodiment of the present invention, illustrating a shoulder on the sidewall of the blood glucose sensor.
Figure 8:
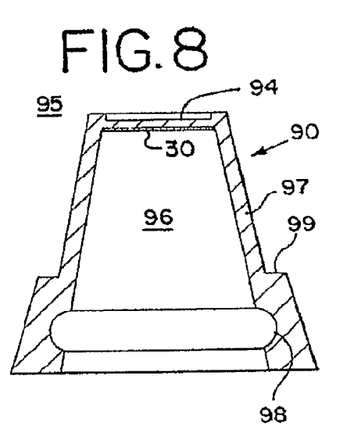
FIG. 8 is a cross-section view of the blood glucose sensor of FIG. 7.

In another embodiment of the present invention, illustrated in FIGS. 7 and 8, the body 90 comprises a porous plastic. The porous plastic of body 90 may be formed similarly to the impermeable plastic of body 12, as described above in connection with the embodiments of FIGS. 1 and 2. The porous plastic is a sintered polymer such as polypropylene, polyvinylidene fluoride, polyethylenevinyl acetate, polystyrene-acrylonitrite, polytetrafluoroethylene or related copolymers. The porous plastic may also be opaque, to reduce the amount of light transmitted through it and increase the amount of light reflected from the sample. The pore size may range from 5 to 100 microns, although other sizes may be used. The porous plastic is hydrophobic so that it resists sample flow unless first treated with a surfactant (not shown). Surfactant may be applied to a sample surface 94 on the outside tip surface 95 of the tip of body 90. Alternately, surfactant may be applied to the inside tip surface 96 of the body 90. To prevent uncontrolled sample flow within the body 90, however, only the reactive area is preferably treated with surfactant. Typical surfactants are derivatives of polyethylene glycol ester, polysorbate, or sorbitan ester.

Sample surface 94 accepts a sample, and can be formed into a concave surface for ergonomic sample loading. A sidewall 97 may extend around the periphery of sample surface 94. A reagent 30, as described above, is applied to the body 90 such that when a droplet of blood reacts with the reagent 30, a color change is caused that can be detected from the inside tip surface 96 of body 90. As illustrated in FIG. 8, the reagent 30 is affixed to the inside tip surface 96 of body 90, opposite sample surface 94. Alternately, the reagent 30 may be affixed to sample surface 94, with surfactant applied to the inside tip surface 96 of body 90. Other aspects of the sensor 90 are similar to the sensor 10 shown in FIGS. 1 and 2 and described above.

FIG. 9 illustrates a blood glucose sensor kit 500 comprising the blood glucose meter 502, a sensor package 550 containing the sensors 10 described above, an alignment guide 540, and an optional removable blood glucose meter cover 530. The blood glucose meter 502 comprises a housing 504, a display 506 for depicting the analyte concentration measured by the meter 502, an optical read-head 510 disposed on the housing 504, and a spring-loaded lancet mechanism 520. As described above, read-head 510 comprises a shape that corresponds to the shape of the sensor 10. An engagement mechanism, such as a push-button ejection mechanism, is located on read-head 510 to detachably engage sensor 10 through first latch 24.

Figure 10:
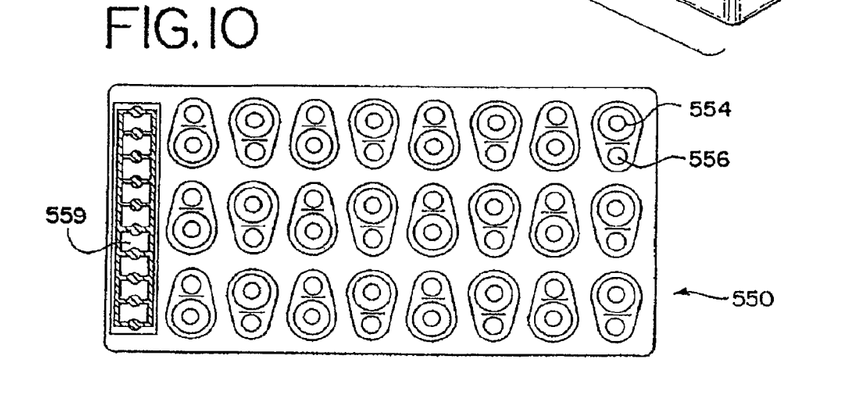
FIG. 10 is a top perspective view of a sensor package used with the blood glucose meter of FIG. 9.

As best seen in FIGS. 10-11, the sensor package 550 comprises a base portion 552, a desiccant material 557, and a protective sheet 558. Sensor cavities 554 are formed as depressions in the base portion 552, with each of the sensor cavities 554 adapted to house an individual sensor 10. As seen in FIG. 11, to prevent or inhibit movement of sensor 10 in the sensor cavity 554, the sensor cavity 554 has an inclined or sloped support wall to position the sensor 10 while it is disposed within the sensor cavity 554. Each of the sensor cavities 554 is in fluid communication with a desiccant cavity 556 formed by a small depression in the base portion 552. Desiccant material 557, such as a 6 mg sphere of Grace 10A molecular sieve desiccant, is disposed in each of the desiccant cavities 556 to maintain an appropriate humidity level to preserve the reagent 30 on the sensor 10. The sensor cavities 554 and desiccant cavities 556 may be aligned in rectangular arrays, allowing for reduced manufacturing and packaging costs.

The protective sheet 558 is attached to base portion 552 such that it seals the individual sensor cavities 554 and desiccant cavities 556, providing a moisture barrier so that the desiccant material 557 can maintain the relative humidity within an optimal range. FIG. 11 illustrates a sensor package 550 design intended for aluminum foil as the protective sheet 558. The sensor cavity 554 is closed by heat-sealing an aluminum burst foil to the surface of the base foil. A typical configuration of this foil is a laminate consisting of a lacquer/8µ aluminium/10µ polypropylene heat-seal material, with an expected shelf life of one to two years for this configuration. One type of foil that can be used for the protective sheet 558 is AL-191-01 foil distributed by Alusuisse Flexible Packaging, Inc. With a tip height of 0.247 inches and a seal width of 0.088 inches, the maximum elongation of the foil is estimated to be 36%.

A conductive calibration label 559 is also disposed on the sensor package 550. The conductive calibration label 559 can be located anywhere on sensor package 550 that space and size constraints allow, for example, on protective cover 558 or on base portion 552. The conductive calibration label 559 provides calibration and production information about the sensor package 550 that can be sensed by calibration circuitry in the blood glucose meter 502. Additional details regarding sensor package 550 are described in U.S. Pat. No. 5,575,403, issued Nov. 19, 1996, and entitled Dispensing Instrument For Fluid Monitoring Sensors, the contents of which are hereby incorporated by reference. One example of such a sensor pack is the Ascensia® AUTODISC™ with ten test strips also available from Bayer Corporation of Elkhart, Ind., United States of America.

Alternatively, sensor package 550 may use a protective sheet 558 made from a thermoformed plastic barrier material. With a thermoformed plastic barrier material, a much greater degree of elongation or stretch is possible. This allows for a more compact package while also accommodating a taller sensor (approximately 0.2" tall). Formable packaging material is available from Klockner-Pentaplast, for example Pentapharm ACLAR PA 300/2. The product, containing ACLAR Ultrx3000, has a Moisture Vapor Transfer Rate (MVTR) of 0.005 g/100 sq in/day at 38° C. and 90% Relative Humidity. With a 6 mg desiccant bead having 15% of available moisture capacity, the expected lifetime of the sensor package 550 is about 45 days.

Referring to FIG. 9, alignment guide 540 is used because the sensors 10 are invisible behind the burst toil of the protective sheet 558. Alignment guide 540 serves to align the read-head 510 with the sensor 10. As shown in FIG. 11, the read-head has two levels of taper, with a step between the two sections. The smaller diameter section 512 of the read-head engages directly with the sensor 10. The larger diameter section 514 is sized to interact with the holes 542 in alignment guide 540 to correctly position the read-head 510 over the sensor 10. A step between the two sections of the read-head 510, with the diameter at the top of the step being slightly larger than the diameter at the base of the sensor, serves to prevent or inhibit the sensor from being caught on the alignment guide as the read-head and attached sensor are withdrawn from the sensor package.

Removable meter cover 530 detachably mounts to blood glucose meter 502, covering the read-head 510 and lancet mechanism 520. The removable meter cover 530 also has a recess adapted to contain the sensor package 550 and alignment guide 540.

To operate a typical blood glucose meter kit 500, the sensor package 550 is stored in the removable meter cover 530 of the blood glucose meter 502 underneath the alignment guide 540 with the calibration label 559 exposed at one end. The sensor package 550 is keyed to ensure the correct orientation within the removable meter cover. Before use, the removable meter cover 530 is removed and the read-head 510 is pushed down through the alignment guide 540 into the sensor package 550 beneath to engage and pick up a sensor 10. The lancet mechanism 520 on the meter 502 is then used to draw a blood droplet that is subsequently applied to the integral first surface 20 of the sensor 10 to start the measurement sequence. After the sequence is completed, the blood glucose measurement is displayed on the meter display 506, the sensor 10 is ejected, and the cover 530 is replaced. With the number of remaining sensors 10 being visible at a glance, an empty sensor package 550 can be easily replaced by raising the alignment guide 540 and removing it from the removable meter cover 530.

Figures 12, 13, 14:
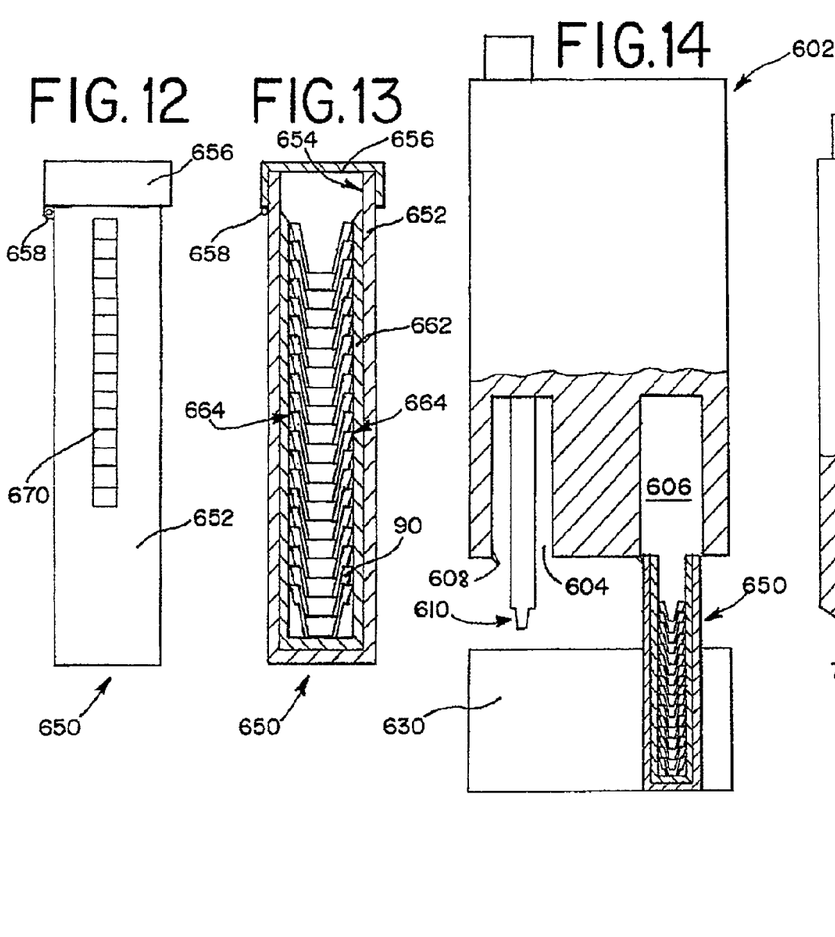
FIG. 12 is a side perspective view of another sensor package.
FIG. 13 is a cross-section view of the sensor package of FIG. 12.
FIG. 14 is a partial cross-section view of another blood glucose kit and the sensor package of FIG. 12.

FIG. 12 illustrates another embodiment of a sensor package 650 for storing a plurality of sensors 90. As seen in FIG. 13, sensor package 650 comprises a container 652 with an inner surface 654, and a cap 656 capable of detachably sealing the container 652. An optional hinge 658 may be connected to the cap 656 and container 652 to allow the cap to open in a flip-top manner. Alternatively, the cap 656 can be fastened to container 652 as a push-on cap, a threaded cap, or by other known methods of attachment. In addition, cap 656 may be a heat sealed or other type of single use lid. A desiccant liner 662 is disposed inside container 652 to maintain an appropriate humidity level to preserve the reagent 30 on the sensor 90. Preferably, desiccant liner 662 is applied to inner surface 654, but may be located anywhere within container 652. A friction liner 664 is also disposed within container 652 so that a plurality of stacked sensors 10 frictionally engages the friction liner 664. Preferably, friction liner 664 is applied to the inner surface of desiccant liner 662 and may be made from any friction material, including any elastic, rubber-like material. Friction liner 664 is intended to exert gentle pressure on the edges of a sidewall 97 to prevent or inhibit movement of the sensors 90 while being engaged by read-head 510. The sensor package 650, depicted as a bottle in FIGS. 12 and 13, may be relatively compact. The embodiment illustrated is sized to hold twenty sensors 90 in a nested array, with a 2 inch height and 0.46 inch diameter, but may be sized to house other numbers or sizes of sensors.

FIG. 13 illustrates a plurality of sensor bodies 90 of FIGS. 7 and 8 positioned within sensor package 650. As described above, sensor body 90 has stepped sidewall 97 such that a shoulder 99 is formed. The shoulder 99 allows sensor body 90 to nest inside another sensor body 90, ultimately forming a nested vertical array of sensors. It should be understood that sensor package 650 may also be used to store the other sensor embodiments disclosed above.

To attach a sensor 90 to the read-head 610, 710 of meter 602, 702 (seen in FIGS. 14 and 15), read-head 610, 710 is pushed down onto a stack of sensors 90 until the latch 98 on the sensor mates with the engagement means (not shown) on the read-head 510. The read-head 510 is then withdrawn with a sensor 90 loaded ready for inoculation with blood. Because of the downward pressure on the stack during mounting, there is a tendency for the sensors to stick together, with the conical outer surface of one sensor binding with the matching conical inner surface of the sensor below. The shoulder 99 of sensor body 90 rests on the top of the sensor body 90 below, and is designed to avoid this binding of successive sensors.

Figure 15:
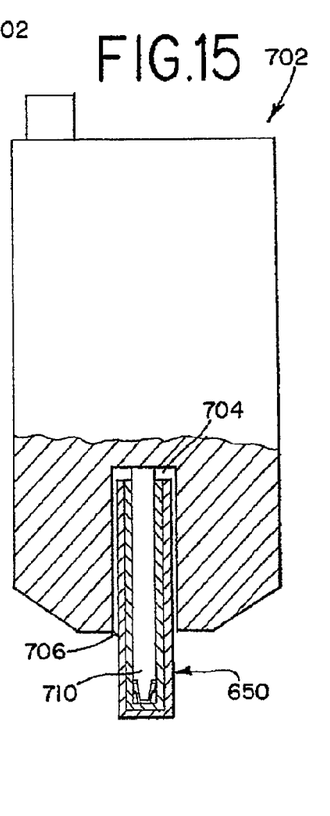
FIG. 15 is a partial cross-section view of an alternate blood glucose instrument and the sensor package of FIG. 12.

FIG. 15 illustrates a meter 702 with read-head 710 and a cover (not shown) removed. The meter 702 is adapted to be used with sensor package 650. For meter 702, sensor package 650 is stored separately from meter 702. The meter 702 contains a bottle cavity 704 concentric with the read-head 710, allowing the read-head 710 to reach down to the bottom of the sensor package 650 and pick out the last sensor 10. A slot (not shown) may also be formed in meter 702 to run almost the length of the bottle cavity 704 to accept the hinge of the bottle. A scribe 706 is positioned on meter 702 to leave a mark on a label 670 that indicates the number of sensors remaining within sensor package 650. The scribe 706 provides for a convenient, instantly visible method of estimating the number of sensors remaining in sensor package 650.

FIG. 14 illustrates another meter 602 with read-head 610 and a cover 630 adapted to store sensor package 650. The meter 602 has two recesses, a bottle cavity 604 concentric with the read-head 610 (described above), and a storage recess 606. When not in use, sensor package 650 is stored within storage recess 606 of the meter 602. A spring-loaded cap (not shown) within the meter 602 seals to the open sensor package 650 to ensure a moisture-proof seal. In operation, to load a sensor 10, the cover 630 is removed from meter 602, rotated 180 degrees and then replaced onto the meter 602, bringing the read-head 610 down into the sensor package 650. After the test is complete (described above), the sensor 10 is ejected and the cover 630 is replaced to seal the sensor package 650 in the storage recess 606. Meter 602 may also position a scribe 608 to leave a mark on a label 670 that indicates the number of sensors remaining within sensor package 650, as described above.

While the invention has been described with reference to details of the illustrated embodiments, these details are not intended to limit the scope of the invention as defined in the appended claims. For example, the sensor may be used for testing fluids other than blood glucose. In fact, the sensor can be used in connection with the analysis of any type of chemical fluid that can be analyzed by means of a reagent material. In addition, the sensors may use sizes, shapes, angles, etc. different than those described above. Further, porous or impermeable plastic body designs may be used with any of the sensor shapes described in FIGS. 1-8. A sensor lid or lid may also be used with porous designs. Moreover, except as noted above, the coloration of the sensor body may be altered such that it is transparent, translucent, or opaque. It is therefore intended to include within the invention all such variations and modifications that fall within the scope of the appended claims and equivalents thereof.

Alternative Embodiment A

A fluid sensor comprising:

a formed plastic body having a tap face with an integral first surface, a bottom face opposed to said first surface, and a sidewall extending from the periphery of said top face, said first surface being adapted to accept a fluid sample; and a reagent, being disposed on said integral first surface and adapted to cause a color change detectable on said bottom face when said reagent reacts with an analyte in said fluid sample.

Alternative Embodiment B

The sensor of alternative embodiment A wherein said formed plastic body is a hollow frustum.

Alternative Embodiment C

The sensor of alternative embodiment A wherein said formed plastic body is a hollow frustum with a larger open end and a smaller closed end.

Alternative Embodiment D

The sensor of alternative embodiment A wherein said sidewall has at least one latch.

Alternative Embodiment E

The sensor of alternative embodiment D wherein said at least one latch is an indentation, hole, groove, or emboss.

Alternative Embodiment F

The sensor of alternative embodiment A wherein said sidewall forms a shoulder.

Alternative Embodiment G

The sensor of alternative embodiment A wherein said color change is measured by a change in reflectance on said bottom face.

Alternative Embodiment H

The sensor of alternative embodiment G wherein said reagent is a glucose dehydrogenase and pyrroloquinoline quinone-based system.

Alternative Embodiment I

The sensor of alternative embodiment H wherein said reagent further comprises an electron transferring mediator, tetrazolium, and formazan.

Alternative Embodiment J

The sensor of alternative embodiment G wherein said reagent is a glucose dehydrogenase and diaphorase-based system.

Alternative Embodiment K

The sensor of alternative embodiment J wherein said reagent further comprises nicotinamide adenine dinucleotide, tetrazolium, and formazan.

Alternative Embodiment L

The sensor of alternative embodiment H wherein said reagent is a titanium dioxide and polymer matrix.

Alternative Embodiment M

The sensor of alternative embodiment I wherein said reagent is a titanium dioxide and polymer matrix.

Alternative Embodiment N

The sensor of alternative embodiment C wherein said frustum has a circular or rectangular cross-section.

Alternative Embodiment O

The sensor of alternative embodiment A wherein said top face has a raised region substantially surrounding said integral first surface.

Alternative Embodiment P

The sensor of alternative embodiment O further comprising a lid attached to said raised region.

Alternative Embodiment Q

The sensor of alternative embodiment P wherein said lid is a rectangular plastic strip, said lid being attached to said raised region forming a plurality of vent openings.

Alternative Embodiment R

The sensor of alternative embodiment P wherein said lid is attached to said raised region and forms a capillary chamber.

Alternative Embodiment S

The sensor of alternative embodiment P wherein said lid is a hollow plastic frustum, having a large open end and a smaller closed end, said smaller closed end having a first surface with a plurality of vent holes.

Alternative Embodiment T

The sensor of alternative embodiment A wherein said top face is transparent.

Alternative Embodiment U

The sensor of alternative embodiment P wherein said top face is transparent or translucent, and said lid is opaque.

Alternative Embodiment V

The sensor of alternative embodiment A wherein said formed plastic body is porous, and further comprises a surfactant applied to said first surface.

Alternative Embodiment W

The sensor of alternative embodiment V wherein said porous plastic body is opaque.

Alternative Embodiment X

The sensor of alternative embodiment U wherein said formed plastic body has a pore size of from about 5 microns to about 100 microns.

Alternative Embodiment Y

The sensor of alternative embodiment A wherein said first surface is concave.

Alternative Embodiment Z

A fluid sensor comprising:
a formed porous plastic body having a top face with an integral first surface, a bottom face with a second surface opposed to said first surface, and a sidewall adjacent to said top face, wherein said first surface is adapted to accept a fluid sample;
a surfactant disposed on said body; and
a reagent adapted to reagent cause a color change detectable on said second surface when said reagent reacts with an analyte in said fluid sample.

Alternative Embodiment AA

The sensor of alternative embodiment Z wherein said reagent is disposed on said second surface and said surfactant is applied to said first surface.

Alternative Embodiment BB

The sensor of alternative embodiment Z wherein said reagent is disposed on said first surface and said surfactant is applied to said second surface.

Alternative Embodiment CC

The sensor of alternative embodiment Z wherein said porous plastic body is opaque.

Alternative Embodiment DD

The sensor of alternative embodiment Z wherein said formed plastic body has a pore size of from about 5 microns to about 100 microns.

Alternative Embodiment EE

The sensor of alternative embodiment Z wherein said top face has a raised region substantially surrounding said integral first surface.

Alternative Embodiment FF

The sensor of alternative embodiment EE further comprising a lid attached to said raised region.

Alternative Embodiment GG

The sensor of alternative embodiment Z wherein said color change is measured by a change in reflectance on said bottom face.

Alternative Embodiment HH

The sensor of alternative embodiment GG wherein said reagent is a glucose dehydrogenase and pyrroloquinoline quinone-based system.

Alternative Embodiment II

The sensor of alternative embodiment HH wherein said reagent further comprises an electron transferring mediator, tetrazolium, and formazan.

Alternative Embodiment JJ

The sensor of alternative embodiment GG wherein said reagent is a glucose dehydrogenase and diaphorase-based system.

Alternative Embodiment KK

The sensor of alternative embodiment JJ wherein said reagent further comprises nicotinamide adenine dinucleotide, tetrazolium, and formazan.

Alternative Embodiment LL

The sensor of alternative embodiment II wherein said reagent is a titanium dioxide and polymer matrix.

Alternative Embodiment MM

The sensor of alternative embodiment KK wherein said reagent is a titanium dioxide and polymer matrix.

Alternative Embodiment NN

A blood glucose sensor kit comprising:
a) a sensor package having:
  i) a base portion having at least one sensor cavity and at least one desiccant cavity in fluid communication with said sensor cavity,
  ii) a desiccant material disposed within said desiccant cavity,
  iii) a protective sheet covering said sensor cavity and said desiccant cavity, and
  iv) a sensor located in said sensor cavity;
b) a blood glucose meter having:
  i) a housing,
  ii) a display disposed on said housing, and
  iii) a read-head disposed on said housing, said read-head being adapted to detachably engage said sensor; and
c) a guide adapted to cover said protective sheet, said guide having at least one opening adapted to align said read-head to engage said sensor within said sensor cavity.

Alternative Embodiment OO

The blood glucose sensor kit of alternative embodiment NN further comprising:

d) a removable blood glucose meter cover detachably mounted to said blood glucose meter, said blood glucose meter cover having a recess adapted to contain said sensor package and said alignment guide.

Alternative Embodiment PP

The blood glucose sensor kit of alternative embodiment NN further comprising a lancet disposed on said housing of said blood glucose meter.

Alternative Embodiment QQ

The blood glucose sensor kit of alternative embodiment NN wherein said protective sheet is thermoformed plastic film or aluminum burst foil.

Alternative Embodiment RR

The blood glucose sensor kit of alternative embodiment NN wherein said sensor package includes a calibration label.

Alternative Embodiment SS

The blood glucose sensor kit of alternative embodiment NN wherein said at least one sensor includes:
  a formed porous plastic body, having a top face with an integral first surface, a bottom face with a second surface opposed to said first surface, and a sidewall adjacent to said top face, wherein said first surface is adapted to accept a fluid sample;
  a surfactant disposed on said body; and
  a reagent being disposed on said body and adapted to cause a color change detectable on said second surface when said reagent reacts with an analyte in said fluid sample.

Alternative Embodiment TT

The blood glucose sensor kit of alternative embodiment NN wherein said at least one sensor includes:
  a formed plastic body, having a top face with an integral first surface, a bottom face opposed to said first surface, and a sidewall extending from the periphery of said top face, wherein said first surface is adapted to accept a fluid sample; and
  a reagent being disposed on said integral first surface and adapted to cause a color change detectable on said second surface when said reagent reacts with an analyte in said fluid sample.

Alternative Embodiment UU

The blood glucose sensor kit of alternative embodiment NN wherein said base portion has a plurality of sensor cavities and at least one desiccant cavity per sensor cavity in fluid communication with said sensor cavity arranged in a rectangular array.

Alternative Embodiment VV

A blood glucose sensor kit comprising:
a) a sensor package having:
  i) a container having an inner surface;
  ii) a desiccant liner disposed in said container;
  iii) a friction liner disposed in said container; and
  iv) at least one sensor located in said container, frictionally engaging said friction liner; and b) a blood glucose meter having:
  i) a housing,
  ii) a display disposed on said housing, and
  iii) a read-head disposed on said housing, said read-head being adapted to detachably engage said sensor while said sensor is located in said sensor package.

Alternative Embodiment WW

The blood glucose sensor kit of alternative embodiment VV wherein said sensor package has a label affixed to an outer surface of said container, said blood glucose meter having a label marker disposed on said housing adapted to mark on said label the depth to which said read-head is inserted into said container.

Alternative Embodiment XX

The blood glucose sensor kit of alternative embodiment VV wherein said blood glucose meter further comprises a lancet disposed on said housing.

Alternative Embodiment YY

The blood glucose sensor kit of alternative embodiment VV further comprising a removable blood glucose meter cover detachably mounted to said blood glucose meter.

Alternative Embodiment ZZ

The blood glucose sensor kit of alternative embodiment VV wherein said removable blood glucose meter cover forms a recess adapted to contain said sensor package.

Alternative Embodiment AAA

The blood glucose sensor kit of alternative embodiment VY wherein said sensor package has a plurality of sensors stacked in an array.

Alternative Embodiment BBB

The blood glucose sensor kit of alternative embodiment VV wherein said desiccant liner is disposed on said inner surface of said container and wherein said friction liner is disposed on said desiccant liner.

Alternative Embodiment CCC

A blood glucose sensor package comprising:
  a) a container having an inner surface;
  b) a desiccant liner disposed in said container;
  c) a friction liner disposed in said container;
  d) a first sensor located in said container, frictionally engaging said friction liner; and
  e) a cover sealing said container.

Alternative Embodiment DDD

The blood glucose sensor package of alternative embodiment CCC further comprising a second sensor located in said container, wherein said second sensor is stacked within said first sensor.

Alternative Embodiment EEE

The blood glucose sensor kit of alternative embodiment CCC wherein said desiccant liner is disposed on said inner surface of said container and wherein said friction liner is disposed on said desiccant liner.

Alternative Method FFF

A method of making a fluid sensor comprising the acts of:
a) forming a plastic body having a top face with an integral first surface, a bottom face opposed to said first surface, and a sidewall extending from the periphery of said top face, wherein said first surface is adapted to accept a fluid sample;
b) applying a reagent to said integral first surface, said reagent being adapted to cause a color change detectable on said bottom face when said reagent reacts with an analyte in said fluid sample; and
c) applying a lid to a raised region on said top face.

The invention claimed is:

1. A system for measuring an analyte concentration of a fluid sample, the system comprising:
 a sensor package including:
  i) a base portion having a plurality of sensor cavities;
  ii) a plurality of test sensors, each test sensor being located in a respective one of the plurality of sensor cavities; and
  iii) a protective sheet covering the plurality of sensor cavities;
 a testing instrument including:
  i) a housing;
  ii) a display; and
  iii) a read-head configured to detachably engage the plurality of test sensors one at a time; and
 an alignment guide configured to cover the protective sheet, the alignment guide having a plurality of apertures, each aperture being configured to align the read-head to detachably engage a corresponding one of the test sensors within the base portion of the sensor package.

2. The system of claim 1, further comprising a removable meter cover having a recess configured to contain the sensor package and the alignment guide where the alignment guide is positioned adjacent the protective sheet.

3. The system of claim 2, wherein the removable meter cover is configured to receive the testing instrument such that a portion of the testing instrument is protected by the removable meter cover.

4. The system of claim 1, wherein the protective sheet is a plastic film or a burstable foil.

5. The system of claim 1, wherein the sensor package further includes a calibration label, the calibration label includes calibration information.

6. The system of claim 1, wherein each test sensor includes a reagent configured to cause a color change when the reagent reacts with an analyte in the fluid sample.

7. A sensor package system, comprising:
 a sensor package including a base forming a plurality of sensor cavities, a plurality of test sensors, each test sensor being located in a respective one of the plurality of sensor cavities, and a protective sheet covering the plurality of sensor cavities;
 an alignment guide configured to at least partially cover the protective sheet, the alignment guide having a plurality of apertures, each aperture being configured to align a meter to detachably engage a corresponding one of the test sensors within the base of the sensor package; and
 a removable meter cover having a recess configured to contain the sensor package and the alignment guide such that the alignment guide is positioned adjacent the protective sheet.

8. The system of claim 7, wherein the removable meter cover further includes a plurality of cavities configured to receive the plurality of sensor cavities of the sensor package.

9. The system of claim 8, wherein when the sensor package is positioned within the recess of the removable meter cover such that each of the sensor cavities of the base is received by a corresponding one of the cavities in the removable meter cover and wherein the alignment guide is positioned within the recess directly adjacent the protective covering, the apertures of the alignment guide are automatically aligned with the sensor cavities of the base.

10. The system of claim 7, wherein the removable meter cover is configured to receive a meter such that the meter is positioned adjacent the alignment guide and a portion of the meter is protected by the removable meter cover.

11. The system of claim 10, wherein the meter includes a housing, a display, and a read-head, the read-head being configured to detachably engage the plurality of test sensors one at a time.

12. The system of claim 7, wherein the sensor package further includes a calibration label, the calibration label being configured to provide calibration information.

* * * * *